United States Patent [19]
Anderson

[11] 4,366,031
[45] * Dec. 28, 1982

[54] ALCOHOL-WATER MIXTURE DISTILLATION

[76] Inventor: Max F. Anderson, Stewardson, Ill. 62463

[*] Notice: The portion of the term of this patent subsequent to Dec. 28, 1999, has been disclaimed.

[21] Appl. No.: 189,313

[22] Filed: Sep. 22, 1980

[51] Int. Cl.³ .............................................. B01D 3/10
[52] U.S. Cl. .................................... 203/18; 202/196; 202/205; 202/234; 202/235; 203/19; 203/91
[58] Field of Search .............. 202/234, 205, 152, 163, 202/164, 167, 176, 177, 181, 182, 185 R, 185 A, 188, 192-196, 198, 232, 233, 235; 203/10, 11, 90, 1, 19, 100, 18, DIG. 17, DIG. 13

[56] References Cited
U.S. PATENT DOCUMENTS

| | | | |
|---|---|---|---|
| 2,490,659 | 12/1949 | Snyder | 202/205 |
| 3,330,740 | 7/1967 | Duffy | 202/205 |
| 4,172,767 | 10/1979 | Sear | 202/234 |

Primary Examiner—Frank Sever
Attorney, Agent, or Firm—Victor R. Beckman

[57] ABSTRACT

Distillation method and apparatus for separation of alcohol from an alcohol-water mixture are disclosed which include use of a fluid-tight vacuum tank within which a surface condenser is located adjacent the tank bottom. The condenser has a vapor inlet above the condenser, and a condenser outlet which communicates with a first pump having a pump discharge outside the tank. A second pump is provided for removal of mixture from the bottom of the tank. In operation, an alcohol-water mixture is fed into the tank to completely fill the same while air is vented therefrom. The vent is closed, and mixture then is pumped from the tank and condenser to empty the condenser and to lower the level of mixture in the tank beneath the vapor inlet to the condenser. With the removal of mixture, a vacuum is created whereupon alcohol rapidly evaporates from the mixture surface to rapidly reduce the temperature of remaining mixture. Alcohol vapor enters the condenser where it is condensed, and the condensed alcohol subsequently is removed from the system by use of said first pump. Gauges are provided for measuring the concentration of alcohol in the mixture, and in the distilled alcohol from the condenser. Means are provided for maintaining the mixture at a predetermined level by the automatic introduction of fresh mixture into the tank in response to the mixture level.

15 Claims, 2 Drawing Figures

ALCOHOL-WATER MIXTURE DISTILLATION

BACKGROUND OF THE INVENTION

Distillation method and apparatus for the distillation and separation of liquid mixtures containing, for example, alcohol are well known. Plain distillation of, say, a mixture of alcohol and water includes the use of a still or retort in which the mixture is heated, and a condenser into which vapor from the still is passed for cooling. Such prior art arrangements require a heat source which contributes substantially both to the cost of the apparatus and to the cost of operating the same. Further, many such distillation means are not well suited for small-scale operation.

SUMMARY OF THE INVENTION AND OBJECTS

An object of this invention is the provision of improved method and apparatus for the distillation of alcohol-water mixtures which are inexpensive and well adapted for small-scale use as by individuals.

An object of this invention is the provision of improved method and apparatus of the above-mentioned type which may be efficiently operated without the use of fuel for heating the mixture for evaporation of alcohol therefrom.

An object of this invention is the provision of an improved intermittent-type vacuum distillation means for use in the distillation and separation of liquid mixtures, such as alcohol-water mixtures, which is mainly operated by use of pumping means.

The above and other objects and advantages are achieved by use of a fluid-tight vacuum tank, or container, into which an alcohol-water mixture is introduced to completely fill the tank while air is vented from the tank. Surface condensing means are located inside the tank adjacent the tank bottom, and condenser inlet means provide communication between the condensing means and the interior of the tank above the condensing means. A condenser outlet provides communication between the condensing means and a pump having a pump outlet outside the tank. When completely filled, some of the mixture is removed from the tank, including all of the mixture in said condensing means, while air is prevented from entering the tank. As a result, a subatmospheric pressure condition is produced inside the tank above the mixture remaining therein. During such mixture removal alcohol evaporates from the surface of the mixture to cool remaining mixture. Alcohol vapor enters the condensing means in the now-cooled mixture through the condenser inlet where it is cooled and condenses. Alcohol is removed from the condensing means, and fresh mixture is introduced into the tank to make-up for alcohol evaporation. Means are provided for measuring the concentration of alcohol obtained from the condensing means for determining the proof thereof. Similar means provide a measure of the concentration of alcohol in the alcohol-water mixture in the bottom of the tank. When the remaining mixture becomes sufficiently dilute, the dilute mixture is removed from the tank and the cycle is repeated. Also, means are provided for pumping contaminated gas from the tank through a second condensing means inside the tank adjacent the tank bottom for removal of the contaminating gas from the tank and for condensing alcohol vapor pumped through the second condensing means with said gas. Means for sensing the level of the mixture of the partially filled tank are provided which control a valve for the introduction of fresh mixture into the tank for automatically maintaining a predetermined mixture level.

The invention, as well as other objects and advantages thereof, will become apparent from the following detailed description when considered with the accompanying drawings.

BRIEF DESCRIPTION OF THE DRAWINGS

In the drawings, wherein like reference characters refer to the same parts in the several views.

Figure 2:
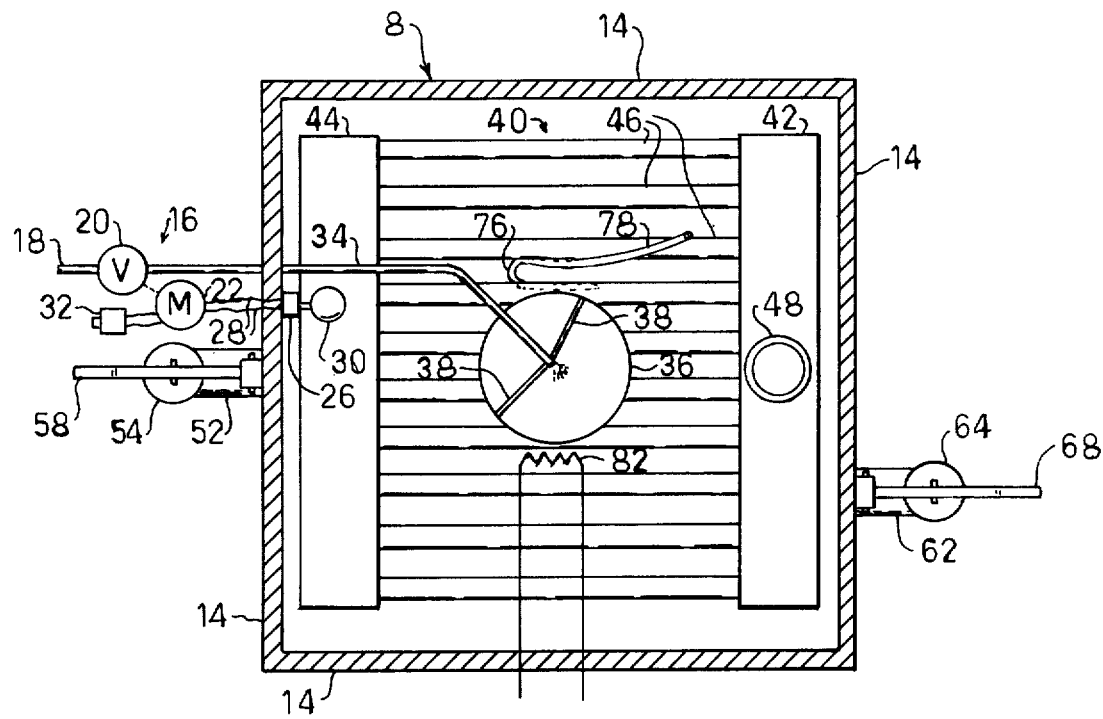
FIG. 2 is a generally diagrammatic sectional view taken substantially along line 2—2 of FIG. 1.

Referring to the drawings, a novel distillation apparatus which embodies the present invention is shown to comprise a fluid-tight vacuum tank, or container, 8 formed with a bottom 10, top 12, and upright side walls 14 extending between the bottom and top members, which tank is supplied with liquid mixture to be separated by distillation. The apparatus is particularly well adapted for the separation of alcohol from a mixture of alcohol and water obtained, for example, by fermentation of carbohydrates, readily available at many farms and factories throughout the world.

Figure 1:
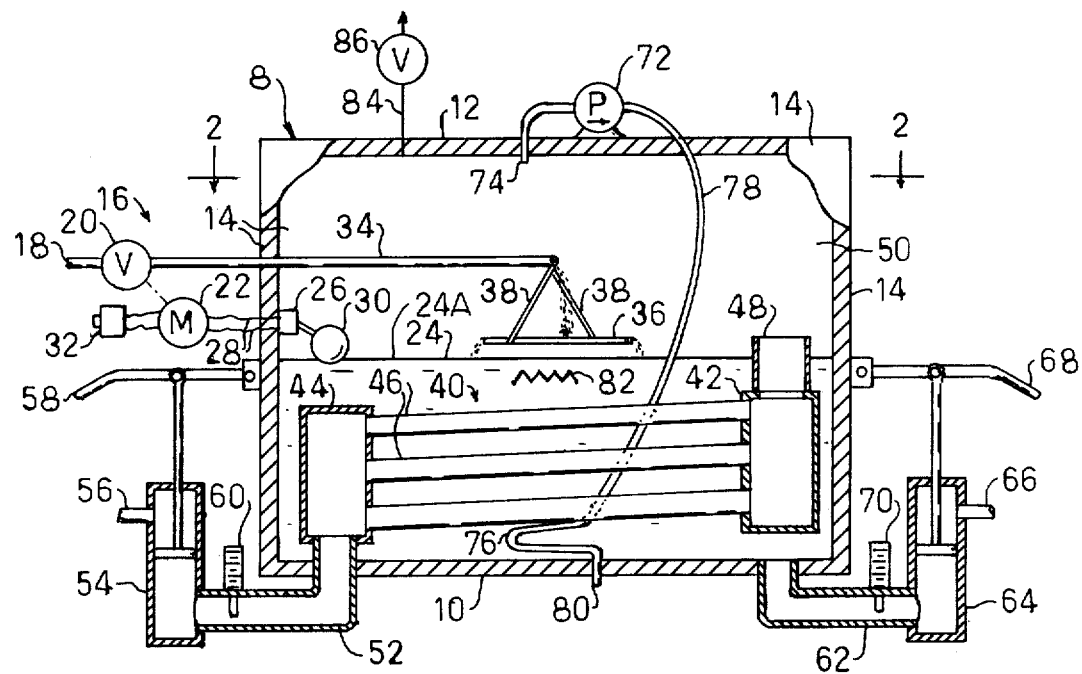
FIG. 1 is a generally diagrammatic side elevational view of a novel distillation apparatus embodying the present invention, with parts shown broken away for clarity.

An alcohol-water mixture to be distilled is fed to the tank from a source, not shown, through a liquid supply system identified generally by reference numeral 16. The illustrated supply system includes a supply line 18 and a valve 20 in the line, which valve is under control of a valve operator motor 22. In FIG. 1, the tank 8 is shown partially filled with mixture 24, and the mixture surface is identified by reference character 24A. The mixture level is automatically controlled by use of a float-operated electrical device 26 connected to the valve operator 22 through lines 28. A float 30 on a pivot arm extending from the device 26 controls the device for control of the valve operator 22 for opening the valve 20 when the float drops below a predetermined level and for closing the valve to shut off the flow of fresh mixture into the vacuum tank when a predetermined mixture level is reached. A manually controlled electrical device 32 also is connected to the valve operator 22 for override control of the float-controlled electrical device 26. It will be understood, then, that the valve 20 may be opened under control of the manually operated control device 32, for completely filling the tank 10 even though the float 30 is in a raised, valve closing, position. As will become apparent hereinbelow, complete filling of the tank with mixture is required for initially establishing a vacuum in the tank at the start of a distillation cycle.

With the valve 20 open, fresh alcohol-water mixture is supplied therethrough to a discharge tube 34 which terminates adjacent the center of the tank above the surface 24A of the mixture 24 at normal level. A deflection plate 36 is located adjacent the end of the discharge tube 34, onto which mixture from the tube is discharged. In the illustrated arrangement the plate 36 is suspended from the end of the tube 34 by use of supporting arms 38. Fresh liquid mixture from the tube 34 falls upon the plate 36 before striking the mixture surface 24A thereby dispersing the fresh liquid over the surface and minimizing the mixing action of fresh mixture with existing mixture.

Alcohol vapor condensing means 40 in the form of a surface condenser is located inside the tank 8 adjacent the bottom 10 beneath the surface 24A of the mixture 24 and, for purposes of illustration, the condensing means is shown to comprise inlet and outlet manifolds 42 and 44, respectively, between which a plurality of vapor tubes 46 extend. An upwardly extending vapor inlet passage, or conduit, 48 at the inlet manifold provides communication between the condenser 40 and the alcohol vapor laden region 50 above the mixture surface 24A. The condenser outlet manifold 44 is connected to an outlet passage, or conduit, 52 extending from the bottom of the tank 8. A pump 54 attached to the conduit 52 is adapted for pumping liquid from the condenser through a pump discharge tube 56 while preventing air from entering the tank through the passage 52. For purposes of illustration, a hand-operated pump 54 of the piston type is shown which pump includes a pivotal pump handle 58 for reciprocal operation of the pump piston. Obviously, other types of pumps, including motor operated pumps, may be used in place of the illustrated hand operated piston pump 54. A gauge 60 is included at the condenser outlet tube to provide a measure of the concentration of alcohol in the condensate from the condenser for determining the proof of the alcohol thereat.

Provision is made for the removal of mixture from the tank 8 through a discharge tube 62 extending from the tank bottom 10. Mixture may be pumped from the tank through the discharge tube 62 by use of a pump 64 which, for purposes of illustration, is shown comprising a hand-operated piston pump similar to pump 54 described above. Mixture is discharged from the pump outlet 66 upon reciprocal movement of the pump piston by operation of the pivotally mounted pump handle 68. Again, any other suitable type of pump may be employed, including a motor operated pump, which pump functions to prevent the entry of air into the tank through the tank discharge tube 62. A gauge 70 is included in the tube 62 for measuring the concentration of alcohol in the alcohol-water mixture thereat. As described in detail hereinbelow, when the alcohol-water mixture becomes too dilute for efficient distillation, the dilute mixture may be removed from the tank using the pump 64.

During operation of the still, gases other than alcohol vapor may accumulate in the tank above the mixture surface. Contaminated gases and vapor may be removed from the region 50 above the surface of the mixture by use of a pump 72 having an inlet tube 74 in communication with the region 50. The pump outlet communicates with a second surface condenser 76 adjacent the bottom of the tank 8 in the mixture 24 through conduit 78. The outlet from the second condenser is connected through conduit 80 to a location exterior of the tank. The pump 72 is operated when it is desired to remove contaminated gases from the tank. By passing the gases through the second condenser 76, alcohol vapor contained therein is condensed, and the condensate drains from the tube 80. Such alcohol may be collected and combined with that obtained from condensing means 40.

If required, heating means may be included in the apparatus for heating the mixture surface 24A to establish the proper pressure-temperature relationship required for evaporation of alcohol from the mixture surface. For purposes of illustration, an electrical heating element 82 is shown which may be connected to an electrical power source, not shown. Obviously, other types of heating means may be used including, for example, heat exchangers supplied with hot water, steam, or the like.

The illustrated distillation system is closed to the atmosphere, and operates at a reduced pressure for so-called vacuum distillation of the mixture; a brief description of which operation now will be given. In accordance with one aspect of the present invention, a reduced pressure condition is effected by first filling the tank 8 with an alcohol-water mixture while venting air from the tank as through a vent line 84 and valve 86 at the top of the tank. The valve operator 22 is controlled by electrical device 32 to maintain the valve 20 open during such initial tank-filling operation as mixture is being supplied through line 18 and now-open valve 20 to the tank. When the tank 8 is completely full, vent valve 86 is closed, and valve operator 22 is controlled by device 32 for closure of the mixture supply valve 20. Opening and closing of the supply valve 20 now is under control of float-controlled device 26 which operates to automatically maintain the mixture at the illustrated predetermined level.

During initial filling of the tank 8, it will be apparent that mixture not only fills the tank, but also enters into the condensing means 40, filling the same. Now, with the tank 8 and condenser 40 filled with mixture and valves 20 and 86 closed, a portion of the mixture is removed by use of pumps 54 and 64. Pump 54 will function for the removal of mixture from the condenser 40 and from the tank 8 to the level of the open upper end of the condenser inlet tube 48. Operation of pump 64 is required for removal of mixture below this level. When the mixture level is reduced below that illustrated, float operated valve 20 opens to restore the mixture to the level illustrated.

While mixture is being pumped from the full tank, a vacuum is created in the tank above the mixture surface resulting in extremely rapid evaporation of alcohol from the mixture and, consequently, rapid cooling of remaining mixture. Cold, dense, mixture flows to the bottom of the tank, providing for a temperature gradient within the mixture such that mixture adjacent the surface where alcohol evaporation takes place is warmer than mixture at the bottom of the tank surrounding the condenser 40. When pumped down to the illustrated level, alcohol vapor filling the region 50 above the mixture surface 24A enters the condenser 40 through the inlet passage 48 where it is cooled and condenses. The alcohol condensate flows from the condenser outlet manifold and into the outlet tube 52 from whence it may be pumped into a suitable receiver, not shown, by use of pump 54. As noted above, the gauge 60 extending into the alcohol in the tube 52 at the condenser outlet provides an indication of the concentration, or proof, of alcohol produced by the distillation system.

As alcohol evaporates from the surface of the mixture, fresh mixture is automatically fed into the tank to maintain the mixture level therein. Mixture entering the tank through feed discharge tube 34 first strikes the deflection plate 36, then flows off the edges of the plate to gently fall upon the surface 24A of the more dilute mixture 24 already in the tank thereby minimizing mixing of the fresh and dilute mixtures. As noted above, a temperature gradient exists in the mixture in the tank, with the temperature at the bottom being lower than the surface temperature for the simultaneous evaporation of alcohol from the warmer mixture surface, and condensation of alcohol vapor within the condenser 40 adjacent the bottom of the tank. By reducing mixing of the fresh and dilute mixtures, as described above, the temperature gradient is least disturbed by the introduction of fresh mixture into the tank, with the warmer fresh mixture remaining at the mixture surface. Also, as noted above, heat may be supplied to the mixture surface as by use of heater 82 for use in establishing the pressure-temperature condition for effective distillation of the mixture.

As distillation continues, the alcohol vapor in region 50 above the mixture surface may become contaminated with other gases. To rid the tank thereof the pump 72 may be operated to pump gases from the tank, through the second condenser 76, and out the condenser discharge tube 80. Alcohol vapor contained therein is condensed in passing through the condenser 76 and may be recovered as it flows from the discharge tube 80.

As alcohol evaporates from the mixture, the mixture, of course, becomes more dilute; with a measure of the strength, or concentration, of the mixture being provided by the gauge 70 in the outlet line 62 from the tank. When the mixture becomes sufficiently dilute, it may be pumped from the tank using pump 64, and the entire distillation cycle repeated beginning with the complete filling of the tank with mixture in the manner described above.

The invention having been described in detail in accordance with requirements of the Patent Statues, various changes and modifications will suggest themselves to those skilled in this art. For example, the tank may be formed with a generally funnel-shaped bottom, the lower end of which terminates in the discharge tube 62 thereby facilitating emptying the tank contents upon operation of the pump 64. Also, mixer blades operable from outside the tank may be included therein adjacent the mixture surface for use in breaking up frozen mixture which may form at the surface when mixture first is withdrawn from the tank to form the vacuum therein. Also, for use in initially filling the tank with mixture, a separate mixture supply means may be provided to avoid having to fill the tank through the float-operated valve 20. It further will be understood that the present, and other prior art, plain distillation processes generally do not produce pure alcohol since other material often evaporates and condenses along with alcohol in the mixture. It will be apparent that the inclusion of other material in the mixture is not precluded so long as a higher concentration of alcohol is obtained by use of the distillation process. Thus terms such as "alcohol", "alcohol vapor", and the like are used in the present application, including the claims, are not intended to limit the invention to the production of pure alcohol. It is intended that the above and other such changes and modifications shall fall within the spirit and scope of the invention as defined in the appended claims.

I claim:

1. In apparatus for distillation of an alcohol-water mixture for recovery of alcohol therefrom, the combination including
   a vacuum tank,
   surface condensing means located inside said tank adjacent the tank bottom,
   condenser inlet means providing communication between said surface condensing means and the interior of the tank above said surface condensing means,
   condenser outlet means extending from said surface condensing means,
   means for filling said tank and surface condensing means with an alcohol-water mixture while venting air from the tank, and
   means in communication with said condenser outlet means for removing a portion of the mixture from the filled tank including all of the mixture contained in said condensing means while preventing entry of air into the tank to produce a subatmospheric pressure condition in the tank for evaporation of alcohol from the mixture surface and cooling of remaining mixture, alcohol vapor passing into said condensing means through said condenser inlet means and condensing therein.

2. In apparatus for distillation of an alcohol-water mixture as defined in claim 1 wherein said means for removing a portion of the mixture from the filled tank also comprises means for removing alcohol condensate from said condensing means.

3. In apparatus for distillation of an alcohol-water mixture as defined in claim 2 wherein said means for removing a portion of the mixture from the filled tank and for removing alcohol condensate from the condensing means comprises a pump.

4. In apparatus for distillation of an alcohol-water mixture as defined in claim 3 wherein said pump is of the manually operated type.

5. In apparatus for distillation of an alcohol-water mixture as defined in claim 1 including a tank outlet at the bottom of the tank, and
   pump means in communication with said tank outlet for removing mixture from the tank to a level beneath the condenser inlet means while preventing entry of air into the tank.

6. In apparatus for distillation of an alcohol-water mixture as defined in claim 5 wherein said pump means also comprises means for removing more dilute alcohol-water mixture from the tank following distillation operation of the apparatus when the concentration of alcohol in the mixture reduces to a predetermined level.

7. In apparatus for distillation of an alcohol-water mixture as defined in claim 6 including means for measuring the concentration of alcohol in mixture at said tank outlet.

8. In apparatus for distillation of an alcohol-water mixture as defined in claim 1 including heating means inside the tank in the alcohol-water mixture adjacent the surface thereof for heating the surface of the alcohol-water mixture.

9. In apparatus for distillation of an alcohol-water mixture as defined in claim 1 including
   means for introducing fresh alcohol-water mixture into the tank in response to mixture level in the tank after a portion of mixture is removed from the tank.

10. In apparatus for distillation of an alcohol-water mixture as defined in claim 1 including
    second surface condensing means inside said tank adjacent the tank bottom having an outlet outside of said tank, and
    means for pumping gases from inside the tank above the mixture level through said second condensing means for removal of contaminated vapor from the tank and condensation of alcohol vapor pumped through said condensing means.

11. In a distillation process for recovering alcohol from an alcohol-water mixture, or the like, comprising
   filling a vacuum tank with a mixture while venting air from the tank,
   removing a portion of the mixture from the filled tank while preventing entry of air into the tank thereby producing a vacuum in the tank above mixture remaining therein,
   evaporating alcohol from the surface of mixture remaining in the tank converting it into alcohol vapor,
   locating condensing means inside the tank adjacent the tank bottom within mixture remaining in the tank, and
   condensing at least a portion of alcohol vapor in said condensing means obtaining alcohol therefrom.

12. In a distillation process as defined in claim 11 including removing alcohol from said condensing means while preventing entry of air into the tank.

13. In a distillation process as defined in claim 11 wherein the step of removing a portion of the mixture from the filled tank includes pumping mixture from the tank through said condensing means to empty said condensing means of mixture.

14. In a distillation process as defined in claim 11 including,
   introducing fresh mixture into the tank in response to mixture level sensing means, following the step of removing a portion of the mixture from the filled tank, for then maintaining mixture at a predetermined level.

15. In a distillation process as defined in claim 11 including
   pumping contaminated gases from said tank through second condensing means located inside said tank adjacent the bottom thereof within mixture remaining in the tank for removal of contaminated gases from the tank and the condensation of alcohol vapor contained in said gases.

* * * * *